United States Patent [19]

Kuessner et al.

[11] 4,330,305
[45] May 18, 1982

[54] REMOVAL OF CO₂ AND/OR H₂S FROM GASES

[75] Inventors: Klaus Kuessner, Frankenthal; Rudolf Irnich, Bobenheim; Hans-Georg Scharpenberg, Hagen; Klaus Volkamer, Frankenthal, all of Fed. Rep. of Germany

[73] Assignee: BASF Aktiengesellschaft, Fed. Rep. of Germany

[21] Appl. No.: 912,355

[22] Filed: Jun. 5, 1978

Related U.S. Application Data

[63] Continuation-in-part of Ser. No. 775,319, Mar. 7, 1977, abandoned.

[30] Foreign Application Priority Data

Mar. 19, 1976 [DE] Fed. Rep. of Germany ....... 2611613

[51] Int. Cl.³ .............................................. B01D 53/14
[52] U.S. Cl. .......................................... 55/48; 55/53; 55/68; 55/73
[58] Field of Search .................. 55/32, 52, 53, 54, 73, 55/89, 48, 68; 423/226, 242, 243

[56] References Cited

U.S. PATENT DOCUMENTS

| | | | |
|---|---|---|---|
| 2,139,375 | 12/1938 | Millar et al. | 55/73 |
| 2,649,166 | 8/1953 | Porter et al. | 55/68 |
| 3,362,133 | 1/1968 | Kutsher et al. | 55/73 X |
| 3,533,732 | 10/1970 | Moore et al. | 55/73 X |
| 3,589,104 | 6/1971 | Panzarella | 55/32 |
| 3,590,555 | 7/1971 | Wackernagel | 55/89 X |
| 3,824,766 | 7/1974 | Valentine et al. | 55/73 X |
| 3,837,143 | 9/1974 | Sutherland et al. | 55/32 |
| 3,915,674 | 10/1975 | Smith | 55/73 X |
| 4,011,066 | 3/1977 | Bratzler et al. | 55/73 X |

FOREIGN PATENT DOCUMENTS

| | | | |
|---|---|---|---|
| 2544569 | 12/1977 | Fed. Rep. of Germany | 55/73 X |
| 1429396 | 3/1976 | United Kingdom | 55/73 |

Primary Examiner—Robert H. Spitzer
Attorney, Agent, or Firm—Keil & Witherspoon

[57] ABSTRACT

Acid constituents, eg. H₂S and CO₂ or their mixtures, are removed from industrial gases or natural gases by means of a washing agent which contains the methyl isopropyl ethers of polyethylene glycols. The washing can be carried out with simultaneous drying of the gas, especially in the case of natural gases, since the anhydrous ethers are able to absorb water.

5 Claims, 2 Drawing Figures

REMOVAL OF CO₂ AND/OR H₂S FROM GASES

This application is a continuation-in-part of our application Ser. No. 775,319, filed Mar. 7, 1977, now abandoned.

The present invention relates to a process for removing $H_2S$ and/or $CO_2$ from gases which contain these constituents, especially as impurities, by washing the gases with a solvent which contains the methyl isopropyl ethers of polyethylene glycols.

The use of organic solvents or aqueous solutions of organic solvents to remove undesired acid constituents, eg. $H_2S$ and $CO_2$, from natural gases and synthesis gases, has been disclosed. A review article in Hydrocarbon Processing, Apr. 1975, pages 84–105, may be mentioned as representative of the extensive prior art.

The solvents for the selective removal of $H_2S$ in the presence of $CO_2$ comprise two groups. Firstly, there are chemical solvents, eg. aqueous solutions of methyldiethanolamine and solutions of salts of α-aminocarboxylic acids, eg. glycine or alanine (Alkazid ®), the selectivity of which is due to the fact that they dissolve $H_2S$ many times more rapidly than they dissolve $CO_2$. Secondly, there are physical solvents, eg. N-methylpyrrolidone (Purisol ®) and the dimethyl ethers of polyethylene glycols (Selexol ®), which thermodynamically dissolve more $H_2S$ than $CO_2$.

In addition to the solubility of a gas in a solvent, from which the minimum amounts of circulating solvent are calculated, the rate of solution of the gas in the solvent is of great importance, since it determines the size of the absorber.

The use of dimethyl ethers of polyethylene glycols or their mixtures to remove $CO_2$ and/or $H_2S$ from gases is disclosed in U.S. Pat. Nos. 2,649,166, 3,362,133 and 3,533,732. German Laid-Open Application DOS No. 2,263,980 discloses alkylpolyethylene glycol tert.-butyl ethers as solvents for acid gases. However only dimethyl ethers of polyethylene glycols have been used as washing agents in commerical plants.

It is true that as a rule the above solvents exhibit adequate absorption of $H_2S$ and/or $CO_2$ and also satisfactory viscosity characteristics; according to the experiments described in German Laid-Open Application DOS No. 2,263,980 the unsymmetrical ethers have somewhat higher absorption capacities than the dimethyl ethers described in the above U.S. Patents. However, the rate of absorption of $H_2S$, both with dimethyl ethers and with methyl tert.-butyl ethers of polyethylene glycols, is not satisfactory in every case.

A further important drawback of the prior art ethers of polyethylene glycols is that they cause corrosion in steel equipment, particularly in the regeneration section of the gas wash. Thus, for instance, it has been observed that the use of dimethyl ethers of polyethylene glycols as washing agent in carbon steel stripping columns of the regeneration section of the gas wash results in a corrosion rate (linear corrosion loss) of up to 0.4 mm p.a., necessitating the use of stainless steel for the regeneration section.

Another disadvantage of prior art solvents is that, when COS is present as an impurity in the gas to be washed, their solubility for COS is unsatisfactory.

It is an object of the present invention to provide a solvent which is less corrosive than the prior art solvents, thus enabling gas washing equipment to be made of ordinary carbon steel. It is another object of the present invention to provide a solvent which not only exhibits a high rate of solution of $H_2S$ but in which $H_2S$ is also adequately soluble. It is still another object of the present invention to provide a solvent having a higher solubility than the above solvents for COS contained as additional impurity in the $H_2S$ and/or $CO_2$ containing gaseous mixtures.

These and other objects and advantages are achieved by a process for removing $H_2S$ or $CO_2$ or both from a gaseous mixture containing $H_2S$ or $CO_2$ or both by washing the gases under pressure with a solvent comprising one or more polyethylene glycol methyl isopropyl ethers containing from 2 to 8 $-[CH_2CH_2-O]-$ units, followed by regeneration of the solvent.

It was surprising that the use of one or more polyethylene glycol methyl isopropyl ethers containing from 2 to 8 $-[CH_2CH_2-O]-$ units instead of, for instance, dimethyl ethers of polyethylene glycols results in a corrosion rate more than four times less than that with prior art solvents, thus enabling gas washing units employing the solvent according to the invention to be made of ordinary carbon steel.

Gases which may be purified in this way are coke oven gases, coal gasification gases, synthesis gases and, preferably, natural gases, from which $H_2S$ is to be removed selectively.

According to the invention, one or more polyethylene glycol methyl isopropyl ethers of the following formula, which contain from 2 to 8 ethylene glycol groups (ie. n=from 2 to 8) are used as solvents:

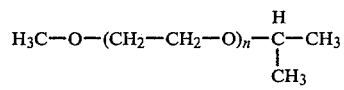

The use of ethers with from 3 to 7 ethylene glycol groups is preferred; from the point of view of the rate of solution of $H_2S$, the compound with 3 ethylene glycol groups, ie. the methyl isopropyl ether of triethylene glycol, has proved best, whereas compounds with 6 to 8 ethylene glycol groups are more suitable for removing $CO_2$. However, in practice mixtures, obtained by synthesizing these compounds in the presence of strongly acid cation exchange resins, are as a rule employed (cf. German Laid-Open Application DOS 25 44 569). If mixtures of monomethyl ethers with 3 to 5 ethylene glycol units are reacted with propylene in accordance with German Laid-Open Application DOS 25 44 569 and the low-boiling constituents are removed, the residual mixtures of monomethyl ethers and methyl isopropyl ethers may be employed as the solvent.

As a rule, the solvents are employed in a virtually anhydrous form. If steam stripping is carried out in the desorption column, the water content of the solvent should not exceed 8% by weight, based on the solvent.

From the point of view of the ability to dissolve $CO_2$ and $H_2S$, the methyl isopropyl ethers of polyethylene glycols behave like physical solvents, ie. Henry's law applies as a good approximation, and thermodynamically more $H_2S$ than $CO_2$ is dissolved.

The process according to the invention is carried out under pressure, advantageously at $H_2S$ partial pressures greater than 0.05 bar and especially greater than 0.5 bar. When removing $CO_2$ from gases not containing $H_2S$, the $CO_2$ partial pressure should advantageously be greater than 4 bars and especially greater than 10 bars. The washing process may be carried out in one stage or two stages. The choice of washing process as a rule depends on the partial pressures of the gases to be washed out and on the final purity required, or on the permissible heat consumption or stripper gas consumption.

The process according to the invention may be carried out either with packed columns or with columns fitted with exchange trays. The temperature of the solvent at the top of the absorber should not exceed 50° C., since, the higher the temperatures, the lower is the gas loading of the solvent. The absorption is as a rule carried out at from 20° to 40° C. The top temperature of the absorber is fixed in accordance with the conventional criteria and as a rule depends on the desired degree of purity and on the temperature of the cooling water.

The rich solvent can be flashed in one or more stages, eg. using a flash turbine, before it is substantially regenerated in a packed desorption column or a desorption column equipped with trays, using stripping gas or steam which can be injected directly or can be generated by adding from 2 to 8% by weight, especially from 3 to 5% by weight, of water to the solvent and employing indirect heat exchange. The solvent can also be stripped with an inert gas.

If, after flashing, the stripping is carried out in a column, it is advantageous to choose a pressure of from 1.1 to 1.5 bars in the main flashing stage.

The solvent running into the desorption column can be heated by means of the solvent discharged, in a countercurrent heat exchanger. The temperature at the bottom of the absorber as a rule is from 110° to 140 C., especially 115° to 130° C. The solvent is conveyed by means of a pump to the top of the absorber via a cooler which can be used to set up the desired top temperature of the absorber.

If the wash is carried out in two stages, only a part of the solvent, coming from the desorption column, is fed to the top of the absorber, while the remainder is fed, at a somewhat higher temperature, to another point of the absorber as it comes from the main flashing stage (cf. FIG. 2).

FIG. 1 shows a one-stage wash. This type of wash is particularly suitable for gases with low partial pressures of the components to be washed out.

Figure 1:
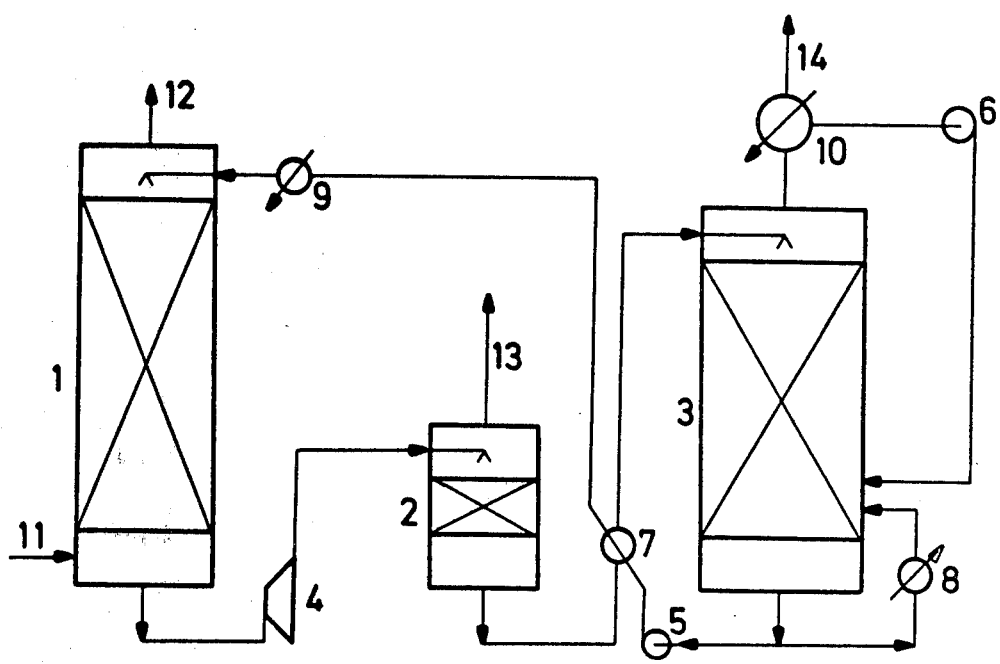
FIGS. 1 and 2 show two preferred process flow charts for carrying out a one-stage wash and a two-stage wash (rough wash and fine wash), respectively.

A rough wash using a flashing circuit may be carried out as follows (cf. FIG. 1):

The gas to be washed is supplied through line 11 to the absorption column 1 through which it flows from bottom to top countercurrent to the solvent which is charged at the top of the column. The washed (treated) gas leaves the absorption column 1 at the top via line 12. The solvent loaded with sour gas leaves column 1 at the bottom and is flashed through a flash turbine 4 into a flash column 2. It is then supplied via heat exchanger 7 to the desorption column 3. The degassed solvent leaves the desorption column at the bottom and is forced by pump 5 via solvent cooler 9 into the top of the absorption column. The flash gas from the flash stage leaves column 2 at the top through line 13. The off-gas from desorption column 3 leaves at the top and is then cooled in offgas cooler 10. The heat balance of the wash is maintained by heat exchanger 8 at the bottom of column 3.

In the Figures, the numbers denote the following:
1. Absorption column
2. Flash column
3. Desorption column
4. Flash turbine
5. Solvent pump
6. Condensate pump
7. Solvent/solvent heat exchanger
8. Reboiler
9. Solvent cooler
10. Off-gas cooler
11. Crude gas
12. Treated gas
13. Flashing gas (inert gas + component washed out)
14. Off-gas (component washed out)

Figure 2:
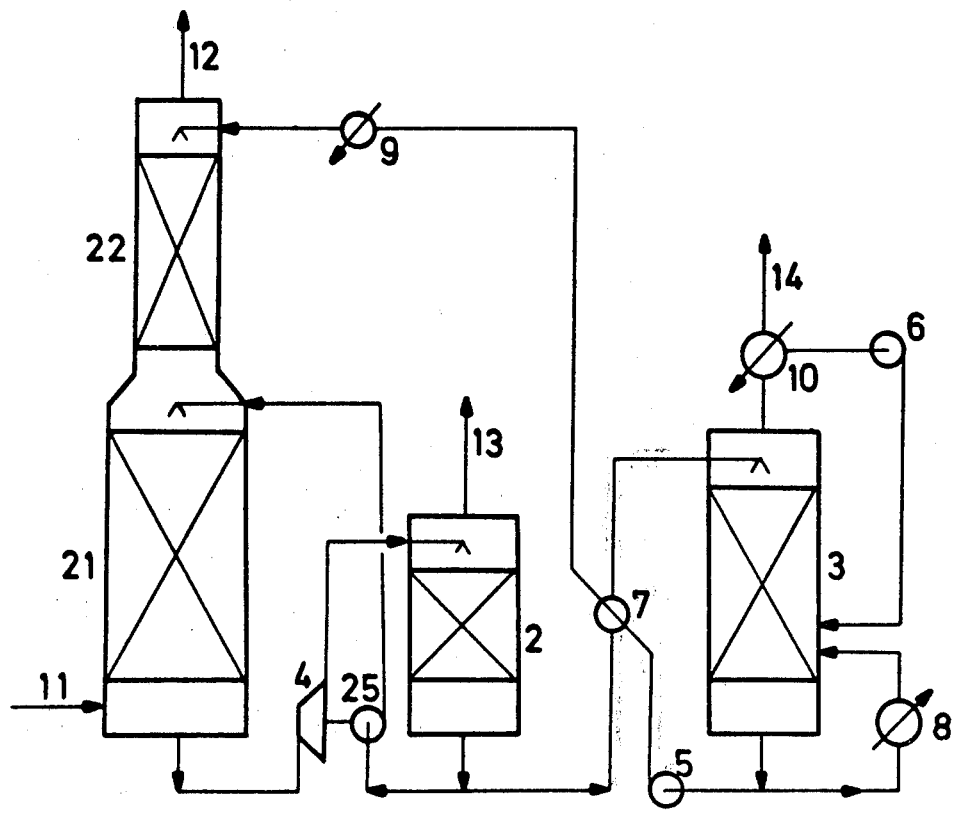

FIG. 2 shows a preferred flow diagram for two-stage washing (rough and fine washing) with one flashing stage and one desorption stage (stripper). The absorption column 1 comprises two sections 21 (rough wash) and 22 (fine wash). The solvent loaded with sour gas is flashed, as in FIG. 1, in turbine 4 and column 2. The solvent leaving flash column 2 at the bottom is divided into two streams. One portion of the stream goes to rough wash column 21 after passing through pump 25, while another portion of the flashed solvent passes through heat exchanger 7 to the top of desorption column 3. Reboiler 8 converts some of the solvent into vapor with which the solvent in column 3 is stripped from sour gas. The solvent stream thus regenerated is pumped by pump 5 through heat exchangers 7 and 9 for cooling, and then fed to fine wash column 22. The off-gas leaving at the top of desorption column 3 is cooled in off-gas cooler 10.

In this Figure, the numbers denote the following:
21. Rough wash column
22. Pine wash column
25. Solvent pump 2.

In addition to their ability to dissolve $H_2S$ and $CO_2$, the methyl isopropyl ethers of polyethylene glycols are able to absorb water. Hence, the solvents to be used according to the invention can also be used for conditioning natural gases. In that case, the water contained in the natural gas would be removed at the top of the stripper (compare position 3 in FIGS. 1 and 2). If the solvent of the invention is used for this purpose, the procedure followed would be as described in German Laid-Open Application DOS No. 2,437,576, which proposes a process for conditioning natural gases by means of solvents other than those now proposed.

The present invention is illustrated by Examples 1 and 2 which follow. Comparative Example 1 compares the rate of absorption of $H_2S$ by methyl isopropyl ethers of polyethylene glycols with the rate of absorption by the ethers mentioned in U.S. Pat. No. 3,362,133 (e) and German Laid-Open Application DOS No. 2,263,980 (f), and Comparative Example 2 the stability of the methyl tert.-butyl ethers of DOS No. 2,263,980 with the methyl isopropyl ethers of the invention.

EXAMPLE 1—Selective $H_2S$ removal 200 m³(S.T.P.)/h of a dry synthesis gas at 16 bars and 50° C. are supplied to a packed column of 0.3 m diameter packed to a height of 7.5 m. The composition of the gas is as follows (in % by vol.):

| | |
|---|---|
| $CO_2$ | 4.0 |
| CO | 46.8 |
| $CH_4$ | 0.2 |
| $N_2$ | 0.2 |
| Ar | 0.4 |

| | |
|---|---|
| H₂ | 48.0 |
| H₂S | 0.4 |
| COS | 24 vol. ppm |

The gas is washed countercurrently with 1.6 m³/h of a solvent comprising 90% w/w of asymmetrical methyl isopropyl ethers of polyethylene glycols [26 wt. % tri, 36 tetra, 23 penta, 11 hexa and 4 hepta], 6% of similarly composed monomethyl ethers and 4% of water, the feed temperature being relatively unfavorable at 50° C. The treated gas leaving the top of the absorber contains 2.9% v/v $CO_2$, 8 vol. ppm of COS and 0.8 vol. % $H_2S$. The wash liquid loaded with sour gas has a temperature of 51° C. at the bottom of the absorber. It is regenerated by flashing to 1.25 bars and stripping with steam in a desorption column (bottoms temperature 130° C.), allowed to cool to 50° and returned to the top of the absorber.

EXAMPLE 2—Joint removal of $H_2S$ and $CO_2$

The method of Example 1 is followed, but 7 m³ (S.T.P.) wash liquid is used per hour. At the top of the absorber the treated gas contains 1200 vol. ppm $CO_2$, <1 vol. ppm $H_2S$ and <8 vol. ppm COS.

COMPARATIVE EXAMPLE 1

Table 1 which follows shows the transfer coefficients Kg for the solvents of the invention and for various solvents of the prior art. The Kg values were determined in a jet stream chamber, the Kg value of the methyl isopropyl ether of triethylene glycol being taken arbitrarily as 1.

TABLE 1

| | relative mass transfer |
|---|---|
| (a) Methyl isopropyl ether of triethylene glycol | 1 |
| (b) Methyl isopropyl ether of tetraethylene glycol | 0.86 |
| (c) Methyl isopropyl ether of pentaethylene glycol | 0.79 |
| (d) Undistilled mixture of a, b and c | 0.72 |
| (e) Mixture of dimethyl ethers of polyethylene glycols with low-boiling constituents | 0.57 |
| (f) Methyl tert.-butyl ether of triethylene glycol | 0.79 |
| (g) Methyl tert.-butyl ether of tetraethylene glycol | 0.58 |

COMPARATIVE EXAMPLE 2

(a) Table 2 which follows shows the results of comparative experiments on the decomposition of the methyl tert.-butyl ether of tetraethylene glycol (A) and of the corresponding methyl isopropyl ether (B) with sulfuric acid. In each case, 30 g of the ether (A) or (B) were heated with 2 drops of concentrated sulfuric acid at 140° C. (A) or 270° C. (B only) for 1 hour. In the case of compound (B), a further 2 drops of concentrated sulfuric acid were afterward added at the higher temperature and the material was heated for a further 2 hours at 270° C. In each case, the isobutene or isopropylene eliminated was determined.

TABLE 2

| Proportion decomposed in % | A | B | |
|---|---|---|---|
| | Amount of concentrated $H_2SO_4$ | | |
| | 2 | 2 | 4 |
| 140° C., after 1 hour | 100% | 0 | — |
| 270° C. after 1 hour | — | 0 | |
| after 3 hours | — | — | 2% |

Table 2 shows that the solvents to be used according to the invention are substantially more stable in an acid medium than the solvents of the prior art, as may be seen from the low degree of decomposition.

(b) In a further experiment, the rate of decomposition of the ethers (A) and (B) was determined. For this purpose, 100 g portions of the ethers were heated with 5% of the acid ion exchanger used for the manufacture of the ether (B) (a sulfonated crosslinked polystyrene resin in the H+ form) at 70° C., and the rate of elimination of olefins was measured. If the rate constant of the decomposition reaction for (B) is taken as = 1, a value of 562 is found for the compounds (A) of the prior art.

EXAMPLE 3

50,000 m³ (S.T.P.)/h of natural gas are treated in a gas treating plant with 88 m³/h of a solvent comprising a mixture of polyethylene glycol methyl isopropyl ethers with 3 to 7 ethylene glycol groups. The composition of the natural gas is as follows (in % by vol):

| | | |
|---|---|---|
| He | 0.05 | |
| $N_2$ | 3.85 | |
| $CO_2$ | 8.88 | |
| $CH_4$ | 80.64 | |
| $C_2H_6$ | 0.19 | |
| $H_2S$ | 6.37 | |
| COS | 150 | vol. ppm |
| $CH_3$—SH | 70 | vol. ppm. |

The absorber temperature is about 0° to 4° C., the absorber pressure is about 80 bars. The laden solvent obtained in the absorber is first flashed to about 20 bars and the flashed solvent is stripped in a stripping column made from carbon steel with steam at about 1.5 bars and 140° C.

The concentration of the sulfur compounds in the scrubbed gas obtained from the absorber is as follows:

| | | |
|---|---|---|
| $H_2S$ | 2.1 | vol. ppm |
| COS | 30 | vol. ppm |
| $CH_3$—SH | 1.1 | vol. ppm |

The corrosion rates in the stripping column (measured as linear corrosion loss in mm p.a. [mm/a]) are as follows:

| section of stripping column | mm/a |
|---|---|
| upper section | 0.07 |
| middle section | 0.09 |
| lower section | 0.08 |

COMPARATIVE EXAMPLE 3

The gas treating plant of Example 3 is operated as indicated in Example 3 except that instead of the mixture of polyethylene glycol methyl isopropyl ethers a mixture of polyethylene glycol dimethyl ethers is used.

The concentration of the sulfur compounds in the scrubbed gas obtained from the absorber is as follows:

| | | |
|---|---|---|
| H₂S | 3.2 | vol. ppm |
| COS | 70 | vol. ppm |
| CH₃—SH | 3 | vol. ppm. |

The concentration of COS and CH₃—SH in the scrubbed gas is more than twice as high as the concentration of COS and CH₃—SH *in the scrubbed gas of Example* 3.

The corrosion rates in the stripping are as follows:

| section of stripping column | mm/a |
|---|---|
| upper section | 0.3 |
| middle section | 0.4 |
| lower section | 0.3. |

The corrosion rate in the stripping column is surprisingly up to 4.4 times higher than when a mixture of polyethylene glycol methyl isopropyl ethers is used as selective solvent.

We claim:

1. A process for removing $H_2S$ or $CO_2$ or both from a gaseous mixture containing $H_2S$ or $CO_2$ or both which comprises washing the gases under pressure with a solvent comprising polyethylene glycol methyl isopropyl ethers containing from 3 to 7 $-(-CH_2CH_2-O-)-$ units, with subsequent regeneration of the solvent.

2. A process according to claim 1, wherein the mixture of polyethylene glycol methyl isopropyl ethers has been obtained by reacting mixing of polyethylene glycol monomethyl ethers containing from 3 to 7 $-(-CH_2CH_2-O-)-$ units in the presence of strongly acid cation exchange resins with propylene.

3. A process according to claim 2 wherein the mixture of polyethylene glycol monomethyl ethers contains from 3 to 5 $-(-CH_2CH_2-O-)-$ units.

4. A process for removing $H_2S$ or $CO_2$ or both from gaseous mixture containing $H_2S$ or $CO_2$ or both which comprises
   (a) contacting said gaseous mixture in a first zone with a solvent comprising a mixture of polyethylene glycol methyl isopropyl ethers containing from 3 to 7 $-(-CH_2CH_2-O-)-$ units to effect absorption of substantially all of the $H_2S$ or $CO_2$ or both and a minor portion of other gases,
   (b) passing the solvent containing the absorbed gases to a second zone maintained at a pressure substantially lower than that in the absorption zone to effect liberation of at least a portion of the absorbed gases,
   (c) withdrawing from said second zone gases liberated therein,
   (d) withdrawing solvent containing $H_2S$ or $CO_2$ or both from said second zone,
   (e) and introducing the solvent to a third zone to effect removal of substantially all of the $H_2S$ or $CO_2$ or both therefrom by heating the solvent or by stripping with steam or inert gases or by heating and stripping,
   (f) returning at least a portion of the desorbed solvent to the top of the absorption zone after adjusting the water content to not more than 8% by weight, based on the solvent, if steam has been added to the solvent in step (e).

5. A process according to claim 4 wherein the mixture of polyethylene glycol monomethyl ethers contains from 3 to 5 $-(-CH_2CH_2-O-)-$ units.

* * * * *